(12) United States Patent  
Bond-Thorley

(10) Patent No.: US 8,931,343 B2  
(45) Date of Patent: Jan. 13, 2015

(54) INSPECTION DEVICE

(75) Inventor: Andrew Bond-Thorley, Stone House (GB)

(73) Assignee: Airbus Operations Limited, Bristol (GB)

( * ) Notice: Subject to any disclaimer, the term of this patent is extended or adjusted under 35 U.S.C. 154(b) by 672 days.

(21) Appl. No.: 12/737,377

(22) PCT Filed: Jul. 24, 2008

(86) PCT No.: PCT/GB2008/050623

§ 371 (c)(1),
(2), (4) Date: Jan. 6, 2011

(87) PCT Pub. No.: WO2010/010317

PCT Pub. Date: Jan. 28, 2010

(65) Prior Publication Data

US 2011/0107837 A1  May 12, 2011

(51) Int. Cl.
  *G01N 29/28* (2006.01)
  *G01N 29/22* (2006.01)
(52) U.S. Cl.
  CPC .............. *G01N 29/28* (2013.01); *G01N 29/221* (2013.01)
  USPC .............................................. 73/617; 73/644
(58) Field of Classification Search
  USPC .................... 73/617, 644, 632, 866.5
  See application file for complete search history.

(56) References Cited

U.S. PATENT DOCUMENTS

| | | | |
|---|---|---|---|
| 4,567,770 A * | 2/1986 | Rumbold et al. ............... | 73/644 |
| 4,651,568 A | 3/1987 | Reich et al. | |
| 4,848,159 A | 7/1989 | Kennedy et al. | |
| 5,031,458 A * | 7/1991 | Young et al. .................... | 73/636 |
| 5,050,436 A * | 9/1991 | Kunii et al. ..................... | 73/644 |
| 5,097,710 A | 3/1992 | Palynchuk | |
| 5,251,487 A * | 10/1993 | Marshall ......................... | 73/644 |
| 5,343,750 A * | 9/1994 | Bashyam ......................... | 73/635 |
| 5,402,791 A | 4/1995 | Saitoh et al. | |
| 5,404,755 A | 4/1995 | Olson et al. | |
| 5,623,107 A | 4/1997 | Patterson, Sr. et al. | |
| 6,039,694 A * | 3/2000 | Larson et al. ................ | 600/459 |
| 6,349,599 B1 * | 2/2002 | Lynnworth et al. ............. | 73/644 |
| 7,637,163 B2 * | 12/2009 | Fetzer et al. .................... | 73/644 |
| 7,694,560 B1 * | 4/2010 | Dam et al. ................. | 73/290 V |
| 2003/0135135 A1 | 7/2003 | Miwa et al. | |

(Continued)

FOREIGN PATENT DOCUMENTS

JP      57-63262 A     4/1982
JP      57-63262 U     4/1982

(Continued)

OTHER PUBLICATIONS

PCT International Preliminary Report on Patentability mailed Feb. 3, 2011 in PCT/GB2008/050623.

(Continued)

*Primary Examiner* — Peter Macchiarolo
*Assistant Examiner* — Rose M Miller
(74) *Attorney, Agent, or Firm* — Nixon & Vanderhye P.C.

(57) ABSTRACT

An inspection device (300) has an ultrasonic transducer (304) encased in a couplant block (302) mounted in a housing (328). The housing (328) has a pair of encoders (340, 342) mounted thereto. The transducer (304) is mounted to scan perpendicular to the contact surface (306) of the block (302). A coupling block with a PTFE layer on the contact surface is also provided.

19 Claims, 6 Drawing Sheets

(56) References Cited

U.S. PATENT DOCUMENTS

| | | | |
|---|---|---|---|
| 2004/0020298 A1* | 2/2004 | Siverling et al. | 73/644 |
| 2004/0050167 A1 | 3/2004 | Linares et al. | |
| 2005/0126293 A1* | 6/2005 | Dasch | 73/618 |
| 2007/0147893 A1 | 6/2007 | Nakatake et al. | |
| 2007/0227249 A1 | 10/2007 | Meier et al. | |

FOREIGN PATENT DOCUMENTS

| | | |
|---|---|---|
| JP | 1291843 | 11/1989 |
| JP | 4-122358 | 4/1992 |
| JP | 7-103952 | 4/1995 |
| JP | 9-49827 | 2/1997 |
| JP | 2004-023863 | 1/2004 |
| JP | 2005-127870 | 5/2005 |
| JP | 2005-315583 | 11/2005 |
| JP | 2006-317417 | 11/2006 |
| JP | 2007-248403 | 9/2007 |
| RU | 2262036 | 10/2005 |
| WO | WO 01/31329 | 5/2001 |
| WO | WO 2008/077566 | 7/2008 |

OTHER PUBLICATIONS

Chinese First Office Action issued Jan. 12, 2012 in CN 200880130464.7 and English translation.
English translation of Chinese Second Office Action issued Aug. 30, 2012 in CN 200880130464.7.
English translation of Russian Office Action in RU 2011104429/28(006239).
Japanese Office Action issued Jan. 8, 2013 in JP 2011-519227 and English summary translation.
International Search Report for PCT/GB2008/050623, mailed Apr. 22, 2009.
Written Opinion of the International Searching Authority for PCT/GB2008/050623, mailed Apr. 22, 2009.
EP Examination Communication dated Jul. 5, 2013 in EP 08788598.4.
Japanese Office Action mailed Dec. 3, 2013 in JP 2011-519227 and English translation.

* cited by examiner

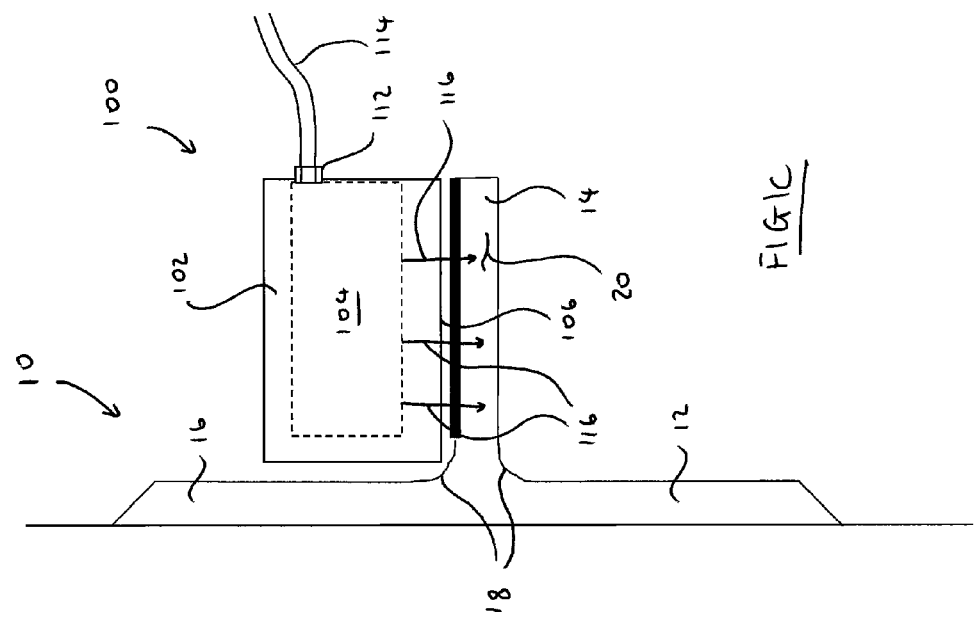
FIG.1c
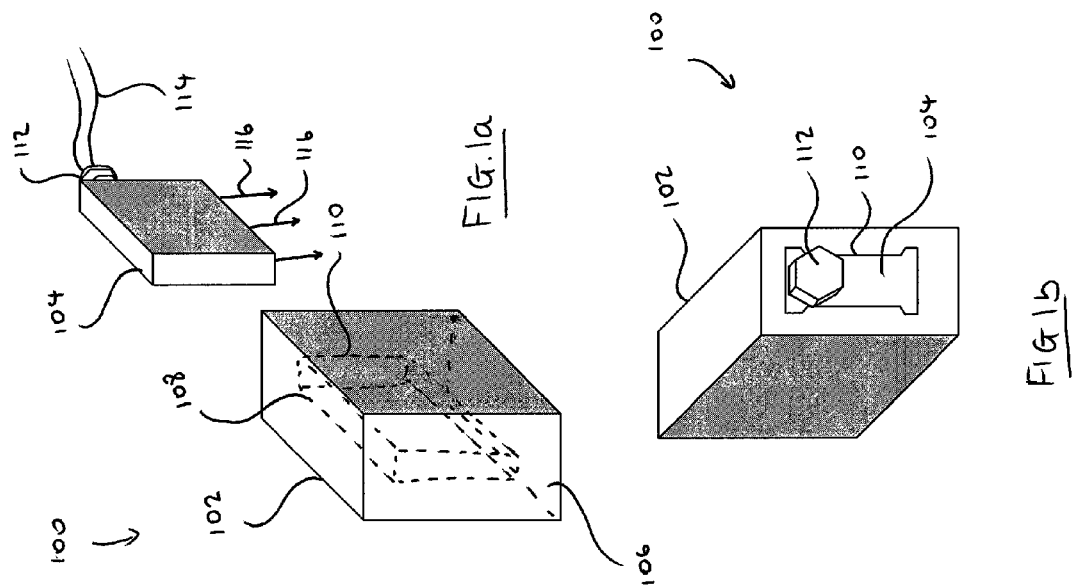
FIG.1a
FIG.1b

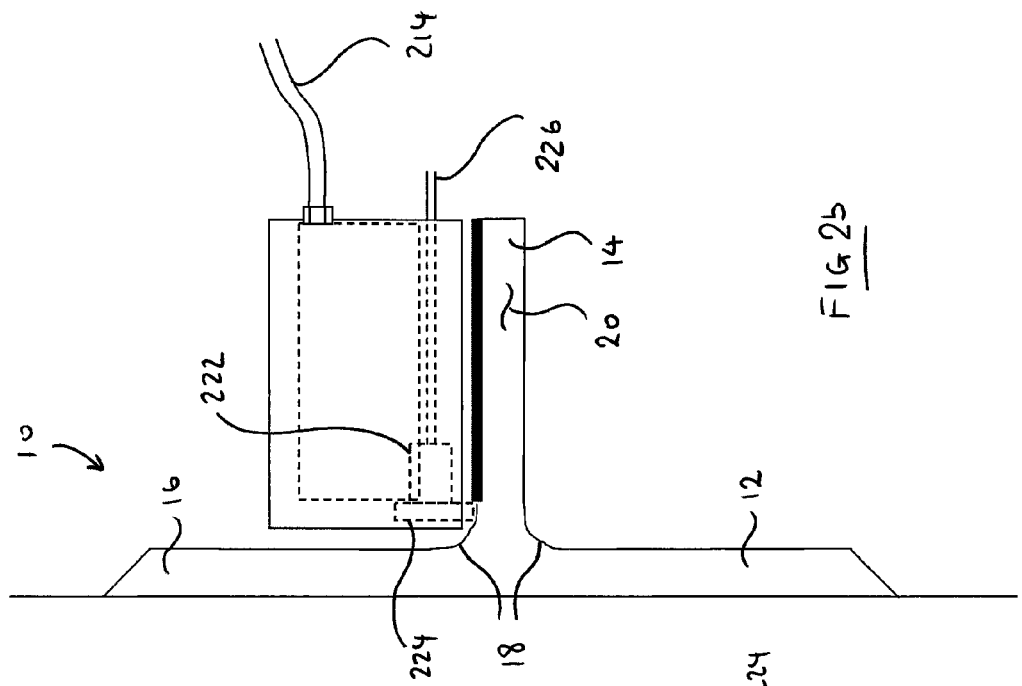
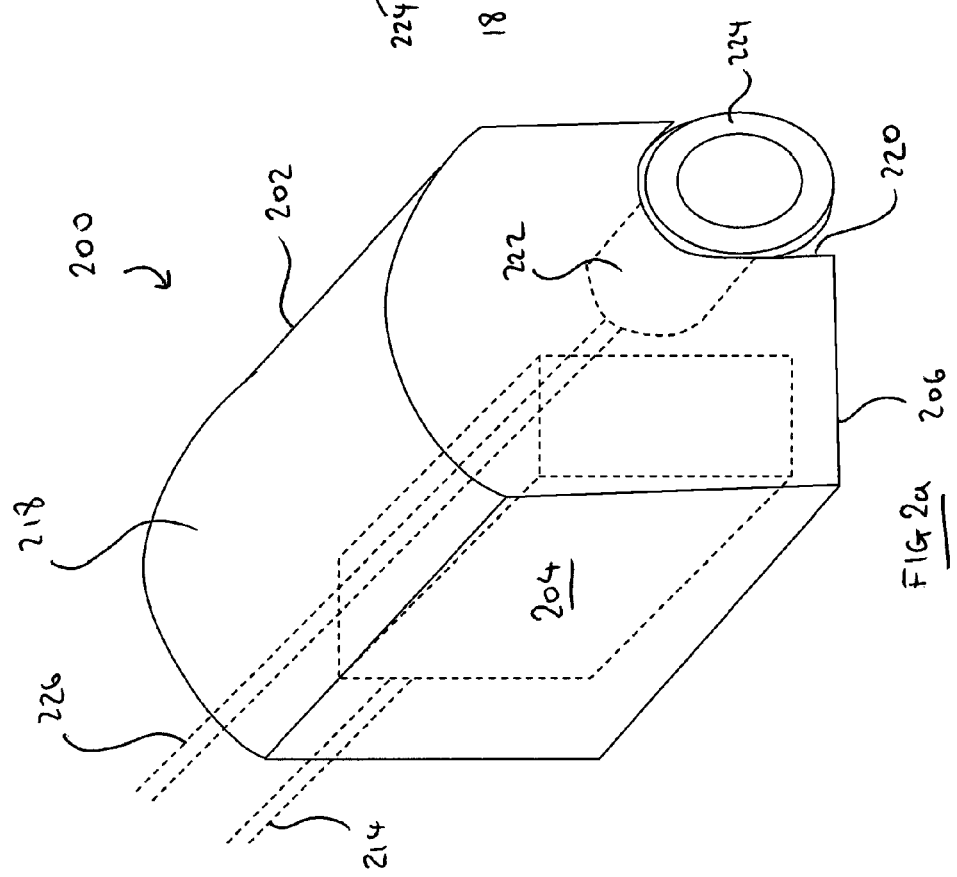

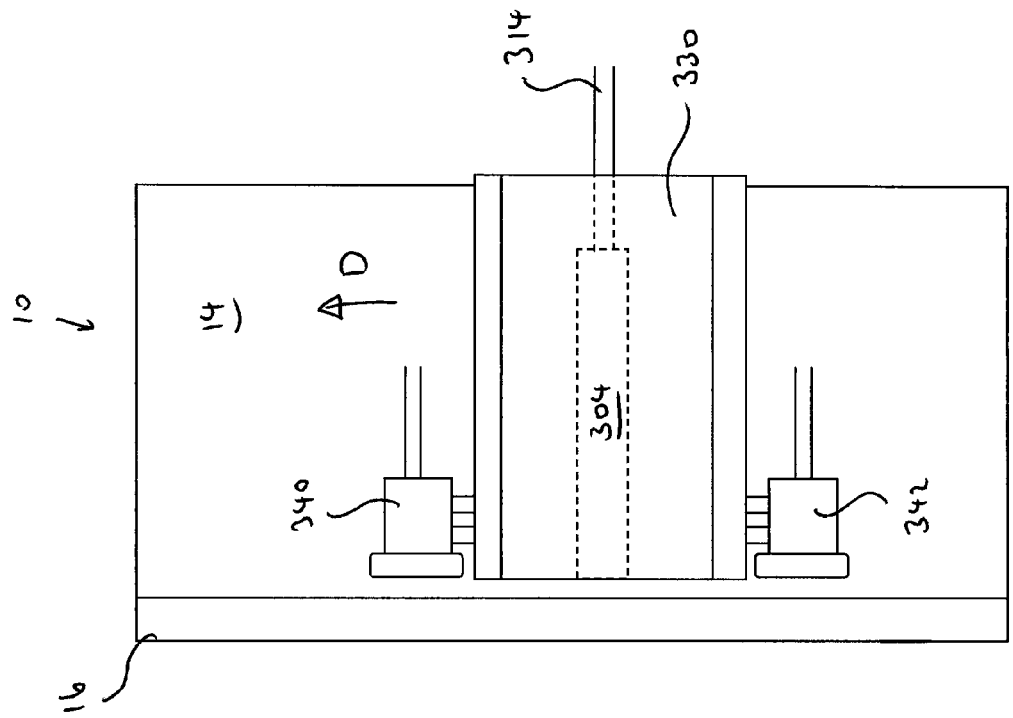
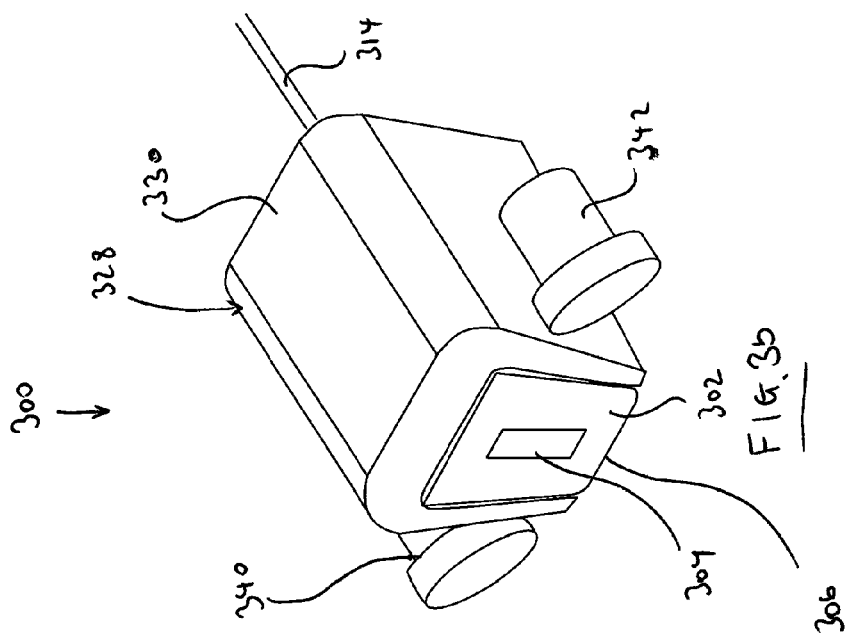

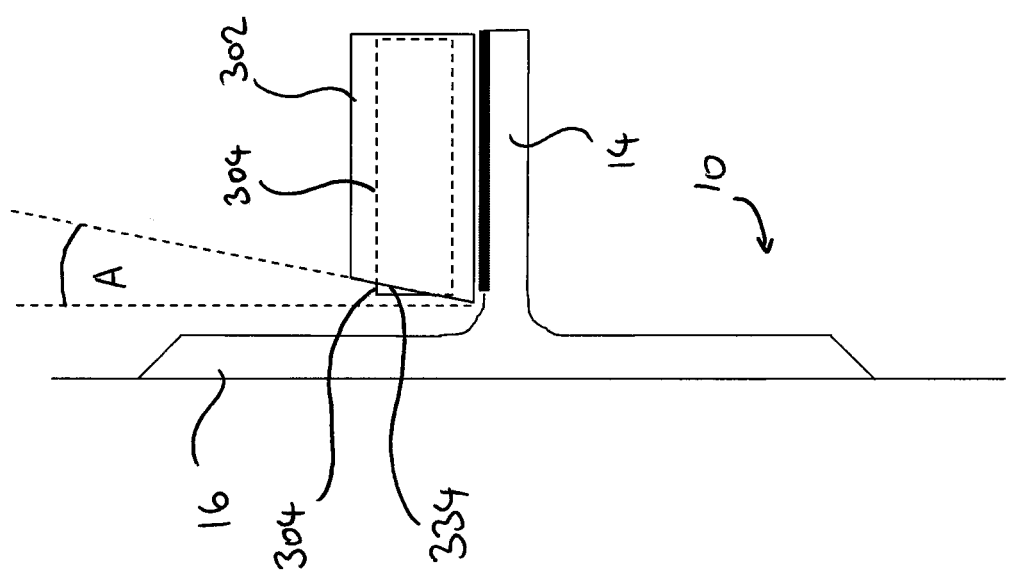

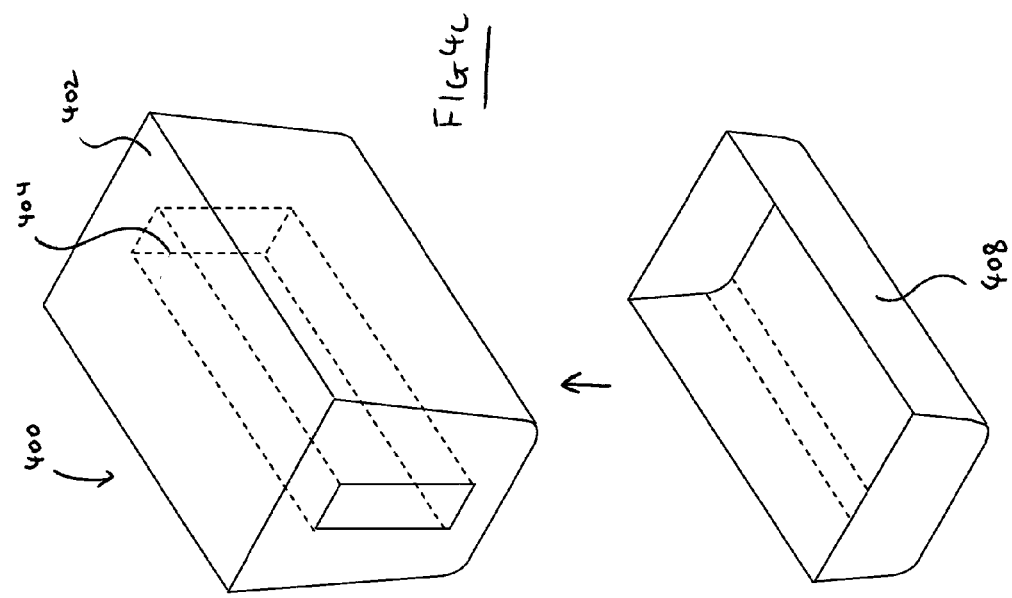
FIG 4c
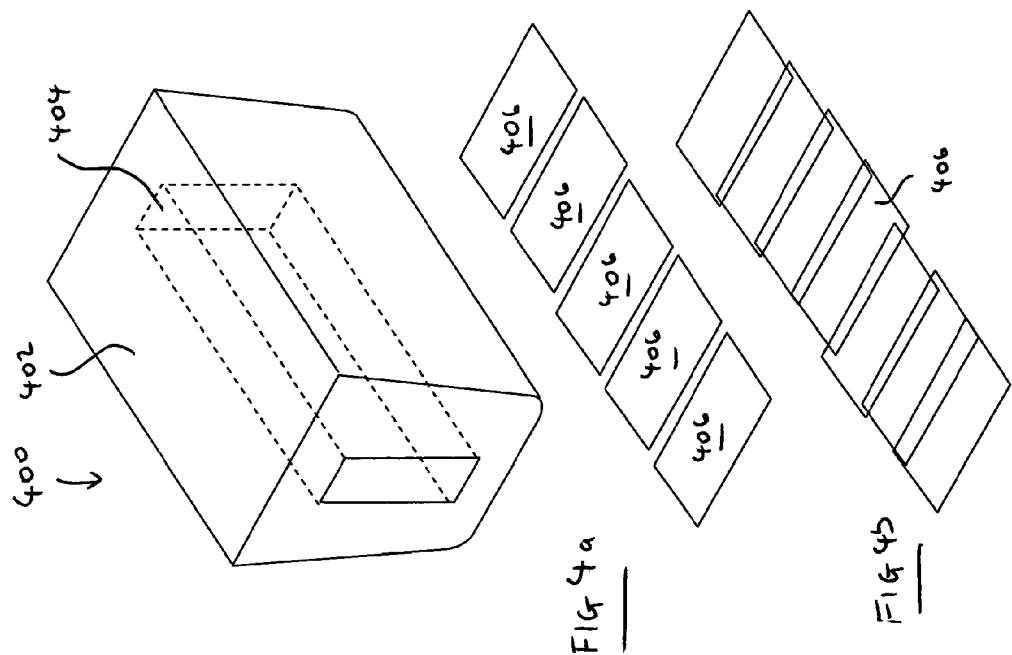
FIG 4a
FIG 4b

INSPECTION DEVICE

This application is the U.S. national phase of International Application No. PCT/GB2008/050623 filed 24 Jul. 2008, which designated the U.S. and the entire contents of which is hereby incorporated by reference.

FIELD OF THE INVENTION

The present invention relates to a device for inspecting components. More specifically, the present invention relates to a device for the ultrasound scanning of composite aircraft components.

BACKGROUND OF THE INVENTION

Non-visible areas of materials, such as the interiors of components, welds and composite materials can be analysed using ultrasonic testing. This type of non-destructive testing (NDT) utilises the reflection of sound waves to detect faults and features which would otherwise be very difficult to detect without destroying the component. Ultrasonic testing is a common technique in the aerospace sector to test the integrity of materials at manufacture and during service.

Scanners tend to be of the portable type (i.e. more suited to in-service scanning) or non-portable type (specifically for production).

A feature of ultrasonic testing is that a couplant is required to aid transmission of the ultrasonic energy to the test specimen because the acoustic impedance mismatch between air and solids (i.e. such as the test specimen) is large. This mismatch causes reflection of the sound waves and a loss in scan quality if a couplant is not used. Couplants generally take the form of water or gel or a deformable solid such as a low acoustic loss elastomer.

Another feature of ultrasonic testing is that the ultrasonic transducer needs to be correctly orientated (usually perpendicularly orientated) with respect to the entity or fault to be detected. In laminar composite materials, these faults exist in a primarily parallel orientation to the surface of the workpiece. As such, correct orientation of the scanner with its scanning direction perpendicular to the surface of the workpiece is important.

Traditionally, ultrasonic testing has been limited in terms of inspection speed as the operation had to be carried out on a point-by-point basis. Improvements have led to the development of array scanning, or "paintbrush" scanning which permits a continuous scan over a surface to produce a two dimensional image of the desired region of the test component. Such equipment however is bulky and limited to use in a production (as opposed to service) environment and is not considered portable.

A problem is that low acoustic loss elastomers have a relatively high coefficient of friction making it difficult to move them across a surface to be scanned. Generally speaking, lower friction materials generally do not have the desired acoustic properties.

It is an aim of the invention to provide an improved inspection device.

SUMMARY OF THE INVENTION

According to the present invention there is provided an ultrasonic scanner for scanning a workpiece comprising:
an ultrasound transducer,
a solid coupling component defining a transducer contact surface for contact with the transducer and a workpiece contact surface for contact with a workpiece to be scanned,
in which the solid coupling component at least partially surrounds the transducer to locate the transducer relative to the workpiece contact surface.

Advantageously, the interface between the transducer and the coupling component acts to orient the transducer correctly with respect to (e.g. normal to) the surface to be scanned.

According to a second aspect of the invention there is provided a coupling component for an ultrasonic scanner comprising a body constructed from an elastomeric polymer and comprising a layer of low friction material at least partially covering the body to form a workpiece contact surface with a coefficient of friction less than 0.5 and preferably approximately 0.1.

Advantageously, a layer of low friction material assists the coupling component in moving across the surface of a workpiece.

By "coefficient of friction" we mean coefficient of friction as measured in the standard way for polymers—i.e. against polished steel.

BRIEF DESCRIPTION OF THE DRAWINGS

An example scanner will now be described in detail with reference to the accompanying figures in which:
FIG. 1a is a perspective view of a first scanner in accordance with the present invention,
FIG. 1b is a perspective view of the scanner of FIG. 1a,
FIG. 1c is a side view of the scanner of FIG. 1a in use,
FIG. 2a is a perspective view of a second scanner in accordance with the present invention,
FIG. 2b is a side view of the scanner of FIG. 2a in use,
FIG. 3b is a perspective view of the scanner of FIG. 3a,
FIG. 3c is a top view of the scanner of FIG. 3a in use,
FIG. 3d is a side view of a part of the scanner of the scanner of FIG. 3a, and
FIGS. 4a-4c are perspective views of low friction coating methods of a fourth scanner in accordance with the present invention.

DETAILED DESCRIPTION OF THE PREFERRED EMBODIMENT

Figure 3A:
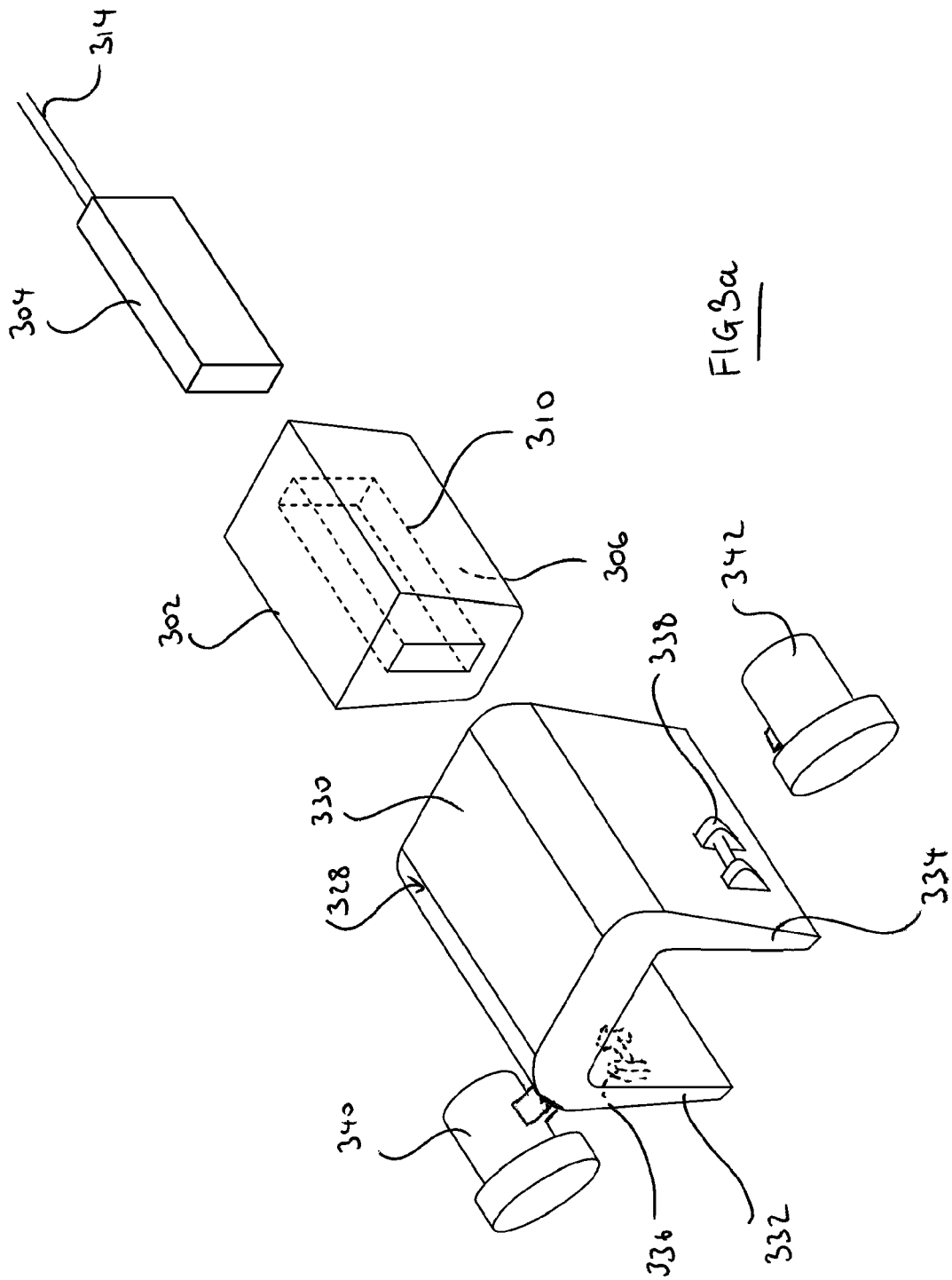
FIG. 3a is an exploded perspective view of a third scanner in accordance with the present invention.

Referring to FIGS. 1a to 1c, a scanner 100 comprises a couplant block 102 and an ultrasound array 104. The couplant block 102 is constructed from a low acoustic loss elastomer, and is generally cuboid shaped. The block 102 defines a workpiece contact surface 106. An array receiving formation 108 in the shape of a cuboidal recess is defined in the block 102 and is open to an insertion orifice 110.

The ultrasound array 104 is of the type well known in the art and is generally cuboidal, comprising a port 112 for connection of a data line 114. The array 104 is capable of emitting and receiving ultrasound in order to scan a component as will be described below. The array has a scanning direction 116.

The scanner 100 is assembled by sliding the array 104 into the array receiving formation 108 through the insertion orifice 110. The array receiving formation 108 is dimensioned to the approximate external dimensions of the array 104, and as such can support the array 104 in a desired position. It is desirable that the scanning direction 116 is perpendicular to the contact surface 106 and as such the receiving formation is oriented with this in mind.

A small amount of couplant liquid (e.g. water or a gel) may be added to the orifice 110 to aid transmission of ultrasound energy across the array-couplant boundary and also to aid insertion and removal of the array 104.

Referring to FIG. 1c, a workpiece 10 comprises a stiffener 12 comprising a flange 14 projecting at 90 degrees to a base 16. The flange 14 joins the base 16 at a pair of opposing fillet radii 18 of 2 degrees radius.

The flange 14 comprises a defect 20 for detection.

To detect the defect 20, the scanner 100 is positioned on the flange 14 with the contact surface 106 fully abutting the flange 14. As such the scanning direction 116 is perpendicular to the flange 14. This provides the optimum orientation between the array 104 and the defect 20 for detection and analysis. Data is collected via the line 114 and analysed appropriately.

The scanner 100 may also be used to detect faults in the base 16.

A fine water spray mist (not shown) is also applied to the scanner and workpiece to reduce friction and increase the efficiency of transmission of ultrasound between the two components.

Turning to FIGS. 2a and 2b, a scanner 200 is shown. Components similar to the scanner 100 are numbered 100 greater.

The couplant block 202 is generally cuboid and comprises an arcuate surface 218 opposite the contact surface 206. The arcuate surface makes the scanner 200 more comfortable to hold in a user's hand.

The couplant block defined a recess 220 in which a rotary encoder 222 is positioned. The rotary encoder 222 comprises an encoder wheel 224 and an encoder data line 226. The encoder 222 is used to determine the distance traveled by the scanner 200.

FIG. 2b shows the scanner 200 in use. Compared to the scanner 100, the scanner 200 uses contact between the encoder wheel 224 and the flange 14 to determine the distance traveled by the scanner 200 over the flange 14. The scanner 200 may also be used to detect faults in the base 16.

Referring to FIGS. 3a to 3c, a scanner 300 is shown. Components similar to the scanner 100 are numbered 200 greater.

The scanner 300 comprises a housing 328 constructed from a plastics material. The housing 328 is generally C-shaped comprising a base portion 330, a first arm 332 and a second arm 334. Each arm 332, 334 defines an encoder mounting arrangement 336, 338 respectively. The housing is ergonomically shaped to be comfortably received in a user's hand.

The scanner 300 comprises a first encoder 340 and a second encoder 342 each similar to the encoder 222. The encoders 340, 342 are mounted to the housing 328 via the encoder mounting arrangements 336, 338. The encoder mounting arrangements 336, 338 are arranged to allow the encoders 340, 342 to move in use but remain resiliently biased towards the workpiece to main contact therewith. Allowing the encoders 340, 342 to move relative to the housing 228 allows the scanner 300 to traverse uneven surfaces with greater effectiveness, as contact is maintained between the contact surface 306 and the workpiece 10.

In use, the housing 328 fits around the couplant block 302 as shown in FIG. 3b. The housing 328 is shaped to retain the couplant block 302 as the first arm 332 and the second arm 334 are tapered inwardly. The arms 332, 334 therefore retain the tapered couplant block 302.

As shown in FIG. 3c, the scanner 300 is moved in direction D along the flange 14 of the workpiece 10. Throughout most of the scanning operation both encoders 340, 342 contact the flange 14, however approaching the ends one of the encoders 340, 342 will lose contact. Under these circumstances, the distance traveled over the flange 14 is determined from a single encoder. In this way, the scanner 300 is capable of scanning the entire length of a workpiece 10. The scanner 100 may also be used to detect faults in the base 16.

FIG. 3d shows a side view of the couplant block 302 of the scanner 300. As can be seen, the couplant block 302 comprises a chamfered end portion 344 of angle A. The end portion 344 therefore allows scanning of flanges 14 at angles of less than 90 degrees to the base 16.

FIG. 4a shows a scanner 400 comprising a couplant block 402 and a transducer 404. The scanner 400 comprises a plurality of flexible self-adhesive PTFE (polytetrafluoroethylene) strips 406. The strips are adhered to the base of the couplant block 402 to provide a low friction layer between the couplant block and a workpiece (not shown).

It has been shown that although PTFE does not generally exhibit favourable acoustic properties for the propagation of ultrasonic waves, using a thin layer of PTFE in the order of 0.05 to 0.2 mm does not significantly inhibit the performance of the scanner.

Turning to FIG. 4b and alternative arrangement is shown whereby the strips of PTFE tape 406 are overlapped.

Turning to FIG. 4c, a PTFE sheath 408 is provided which conforms substantially to the exterior profile of the couplant block 402. As such an even layer of PTFE is provided which eliminates any effects that may be caused by having the edges of the PTFE tape 406 in the scanning field.

The invention claimed is:

1. An ultrasonic scanner for scanning a workpiece comprising:
   an ultrasound transducer including an outer surface and a scanning direction, said transducer comprising an array line; and
   a solid coupling component including an orifice corresponding to an outer shape of said transducer outer surface, said orifice extending into said component in a direction perpendicular to said scanning direction, said transducer located at least partially in said orifice, said orifice including a transducer contact surface between said component and said transducer and a workpiece contact surface for contact between said component and said workpiece, wherein said array line is parallel to the transducer contact surface.

2. An ultrasonic scanner according to claim 1 in which the transducer contact surface and the workpiece contact surface are substantially planar and substantially parallel.

3. An ultrasonic scanner according to claim 1, wherein the transducer outer surface comprises a substantially prismatic outer surface and the orifice has a corresponding prismatic shape to receive the transducer.

4. An ultrasonic scanner according to claim 1 in which the transducer comprises a polygonal cross section and said orifice has a corresponding polygonal cross section shape to receive the transducer.

5. An ultrasonic scanner according to claim 1 comprising a layer of low friction material at least partially covering the workpiece contact surface with a coefficient of friction less than 0.5 as measured against polished steel.

6. An ultrasonic scanner according to claim 5 in which the low friction material has a coefficient of friction of approximately 0.1.

7. An ultrasonic scanner according to claim 6 in which the low friction material is polytetrafluoroethylene (PTFE).

8. An ultrasonic scanner according to claim 5 in which the low friction material is in the form of an adhesive tape.

9. An ultrasonic scanner according to claim 1 further comprising a housing to which the coupling component is mounted, the housing defining a surface for gripping by a user in use.

10. An ultrasonic scanner according to claim 1 further comprising a first encoder mounted to the scanner to contact a workpiece and determine distance traveled relative thereto in use.

11. An ultrasonic scanner according to claim 10, comprising a second encoder mounted on a side of the scanner opposite to the first encoder.

12. An ultrasonic scanner according to claim 11 in which at least one of the first and second encoders is resiliently mounted to the scanner to reside towards a workpiece.

13. A coupling component for an ultrasonic scanner comprising a body constructed from an elastomeric polymer and comprising a layer of low friction material at least partially covering the body to form a workpiece contact surface with a coefficient of friction less than 0.5 as measured against polished steel.

14. A coupling component for an ultrasonic scanner according to claim 13 in which the low friction material has a coefficient of friction of approximately 0.1.

15. A coupling component for an ultrasonic scanner according to claim 14 in which the low friction material is polytetrafluoroethylene (PTFE).

16. A coupling component for an ultrasonic scanner according to claim 13 in which the low friction material is in the form of an adhesive tape.

17. A coupling component for an ultrasonic scanner according to claim 13 in which the low friction material is in the form of a sheath around at least a part of the coupling component.

18. A coupling component for an ultrasonic scanner according to claim 13 in which the low friction material layer has a thickness of 0.05 to 0.2 mm.

19. An ultrasonic scanner for scanning a workpiece comprising:
    an ultrasound transducer,
    a solid coupling component defining a transducer contact surface for contact with the transducer and a workpiece contact surface for contact with a workpiece to be scanned,
    in which the solid coupling component at least partially surrounds the transducer to locate the transducer relative to the workpiece contact surface, comprises a layer of low friction material at least partially covering the workpiece contact surface with a coefficient of friction less than 0.5.

* * * * *